(12) United States Patent
Huang et al.

(10) Patent No.: US 10,004,438 B2
(45) Date of Patent: Jun. 26, 2018

(54) IMPLANTABLE REAL-TIME OXIMETER TO DETERMINE POTENTIAL STROKES AND POST-TRAUMATIC BRAIN-INJURY COMPLICATIONS

(71) Applicant: University of Rochester, Rochester, NY (US)

(72) Inventors: Jason Haitao Huang, Temple, TX (US); Samantha Dayawansa, Temple, TX (US)

(73) Assignee: University of Rochester, Rochester, NY (US)

( * ) Notice: Subject to any disclaimer, the term of this patent is extended or adjusted under 35 U.S.C. 154(b) by 0 days. days.

(21) Appl. No.: 14/395,494

(22) PCT Filed: Mar. 14, 2013

(86) PCT No.: PCT/US2013/031236
§ 371 (c)(1),
(2) Date: Oct. 19, 2014

(87) PCT Pub. No.: WO2013/158271
PCT Pub. Date: Oct. 24, 2013

(65) Prior Publication Data
US 2015/0073240 A1 Mar. 12, 2015

Related U.S. Application Data

(60) Provisional application No. 61/636,299, filed on Apr. 20, 2012.

(51) Int. Cl.
*A61B 5/1455* (2006.01)
*A61B 5/1459* (2006.01)
(Continued)

(52) U.S. Cl.
CPC .......... *A61B 5/1459* (2013.01); *A61B 5/0205* (2013.01); *A61B 5/14552* (2013.01);
(Continued)

(58) Field of Classification Search
CPC .............. A61B 5/1459; A61B 5/14542; A61B 1/00165; A61B 5/028; A61B 5/1455;
(Continued)

(56) References Cited

U.S. PATENT DOCUMENTS 4,805,623 A * 2/1989 Jobsis ................ A61B 5/14551
250/339.12
5,205,292 A * 4/1993 Czar ........................ A61B 8/12
600/459
(Continued)

FOREIGN PATENT DOCUMENTS

WO WO 8906513 A * 7/1989 ............... A61B 5/02

*Primary Examiner* — Eric Winakur
*Assistant Examiner* — Chu Chuan (J J) Liu
(74) *Attorney, Agent, or Firm* — Robert D. Gunderman, Jr.; Patent Technologies, LLC

(57) ABSTRACT

A first embodiment of the implantable real-time oximeter of the present invention is attached around a blood vessel near the site of a likely stroke to monitor large and medium size cerebral arteries. Another embodiment of the implantable real-time oximeter can be passed within cerebral blood vessels to monitor the oxygenation status of the surrounding cerebral tissues. When used within cerebral blood vessels, the emitter and detector are coplanar and contained in a small area, for example, 50-120 μm.

5 Claims, 8 Drawing Sheets

(51) Int. Cl.
*A61B 5/0205* (2006.01)
*A61B 5/00* (2006.01)
*A61B 5/024* (2006.01)

(52) U.S. Cl.
CPC .......... *A61B 5/6876* (2013.01); *A61B 5/6884* (2013.01); *A61B 5/6885* (2013.01); *A61B 5/02433* (2013.01); *A61B 2562/0238* (2013.01)

(58) Field of Classification Search
CPC ............ A61B 5/14551; A61B 5/14532; A61B 5/14552; A61B 5/6876; A61B 5/6883; A61B 5/6884; A61N 1/36557
See application file for complete search history.

(56) References Cited

U.S. PATENT DOCUMENTS

| | | | | |
|---|---|---|---|---|
| 5,598,841 A * | 2/1997 | Taniji | ................... | A61B 5/0261 600/342 |
| 5,995,860 A * | 11/1999 | Sun | ...................... | A61B 5/1459 600/316 |
| 6,049,727 A * | 4/2000 | Crothall | ............. | A61B 5/14532 600/310 |
| 6,106,477 A * | 8/2000 | Miesel | ................. | A61B 5/0215 600/486 |
| 6,487,428 B1 * | 11/2002 | Culver | ................. | A61B 5/0084 600/310 |
| 2002/0156353 A1 * | 10/2002 | Larson | ............... | A61B 5/14552 600/323 |
| 2008/0045822 A1 * | 2/2008 | Phillips | ................ | A61B 5/1459 600/323 |
| 2008/0119911 A1 * | 5/2008 | Rosero | .................... | A61N 1/05 607/62 |
| 2009/0093729 A1 * | 4/2009 | Zhang | ................ | A61B 5/02007 600/486 |
| 2009/0240125 A1 * | 9/2009 | Such | .................. | A61B 5/14552 600/323 |

\* cited by examiner

IMPLANTABLE REAL-TIME OXIMETER TO DETERMINE POTENTIAL STROKES AND POST-TRAUMATIC BRAIN-INJURY COMPLICATIONS

RELATED APPLICATION

This application claims priority to U.S. Provisional Patent Application No. 61/636,299, filed Apr. 20, 2012, whose disclosure is hereby incorporated by reference in its entirety into the present disclosure.

FIELD OF THE INVENTION

The present invention is generally related to a pulse oximeter and more particularly to a pulse oximeter that can be implanted onto a large or medium sized blood vessel or that can be inserted into a medium or a small blood vessel such as a cerebral blood vessel to measure cerebral tissue oxygenation.

Background of the Invention

Pulse oximetry is a technique for monitoring the oxygenation of a patient's hemoglobin. A sensor is placed on a thin part of the patient's body, usually a fingertip or earlobe, or in the case of an infant, across a foot. Light of two different wavelengths, typically red and infrared, is passed through or reflected by the patient's blood to a photo detector. The changing absorbance at each of the provided wavelengths is measured, allowing for the determination of absorbances due to the pulsing arterial blood alone, excluding venous blood, skin, bone, muscle, and fat. From the absorbances, the ratio of oxygenated to deoxygenated hemoglobin can be determined.

Above the skin, pulse oximetry has long been used to detect hypoxic situations, but is limited in it's range of diagnostic capabilities.

For example, currently available pulse oximeters cannot be used to measure the oxygenation status of cerebral tissues.

An implantable pulse oximeter is taught in Reichelt et al, "Development of an Implantable Pulse Oximeter," *Transactions in Biomedical Engineering*, Vol. 55, No. 2, February 2008, pp. 581-588. That article also suggests the use of telemetry to transmit the signal from the detector to an external unit. However, there is no teaching to use the oximeter for stroke or other brain conditions and the oximeter taught therein cannot be miniaturized enough for use on blood vessels near the likely location of a potential stroke. The device has not been tested in vivo.

Hickey et al., 2011, *Journal of Clinical Monitoring and Computing* (2011) 25:245-255 describes a single plane oximeter.

In cardiology, there are devices such as Holter monitors to detect rhythm differences in an ambulatory patient. There is no such similar device to monitor cerebral perfusion.

SUMMARY OF THE INVENTION

It is thus an object of the invention to provide an implantable pulse oximeter for implantation in the blood vessels which can give rise to a stroke (as exemplified by the first preferred embodiment, or Oximeter A) and another (as exemplified by the second preferred embodiment, or Oximeter B) which will have the ability to be passed within a cerebral blood vessel to measure oxygenation of deep brain areas.

Oximeter A will be tested using a large rodent vessel, a large rodent vessel. The device will have a diameter of 1-3 mm. The design will be miniaturized in stages to embrace human carotid or major cerebral arteries or major cerebral artery branches.

At the same time, oximeter B, a single plane oximeter, in which the light emitter and the detector are in the same plane, will also be tested.

The second device will be used to measure tissue oxygenation levels by measuring capillary oxy/deoxy Hemoglobin levels.

Oximeter B will be miniaturized to a size in the range of 125-150 μm. Since oxygen measuring probes as small as 125 μm are known, this target size is feasible. The light source and the detector are coplanar such that the oximeter works by reflection. The oximeter is made of biocompatible materials to avoid immunorejection and will allow for direct attachment to an inner wall of a blood vessel. The output signal of the device will provide for the oxygenation status of the surrounding brain tissues.

Output signals from both of the above devices can in turn be sent to a telemetry unit to provide remote monitoring of the condition of an ambulatory patient.

The oximeter of device A can be implanted to monitor for a potential stroke. It can be used for high-risk populations and to assess the need for preemptive treatment.

The present invention uses known pulse oximetry principles. The device of the present invention uses the ratio of red and infrared absorption of oxy and deoxy hemoglobin to measure the hemoglobin saturation of oxygen. Current pulse oximeters are non-invasive, and there are no known side effects.

In one embodiment, a semicircular red and infrared light emitter and a semicircular light receptor are used to make the oximeter A. They will face each other embracing the blood vessel. Considering the biconcave shape of the red blood cell, such an assembly will provide good readings.

The design of Oximeter B is as follows. Infrared and red light sources will be used along with a single light receptor, in which all three will be in the same plane. Oximeter B will be capable of passing through cerebral vessels with or without CT (computer tomography) guidance. Oximeter B will measure the oxygen saturation of the hemoglobin in capillaries of adjoining cerebral tissues, without being invasive to those adjoining cerebral tissues. In one embodiment, a 50 μm diameter sensor is provided to reach deep brain areas angiographically, using fiber optic light sources and absorption fibers.

In another embodiment, both devices incorporate wireless telemetry. This will allow patients as well as medical personnel to monitor those patients and intervene as soon as the need arises.

Applications include:

1) Monitor patients for complications following traumatic brain injury.

2) Post stroke monitoring of the patient to prevent recurrent strokes.

3) Diagnose the potential for stroke

4) Monitor patients with vascular insufficiencies (transient ischemic attack, carotid stenosis, basilar artery insufficiency, peripheral arterial diseases, mesenteric ischemia, etc.).

5) Monitor patients with pulmonary insufficiencies (pulmonary embolism, asthma, pulmonary edema), 6) Monitor patients with cardiac insufficiencies.

7) Monitor fetuses and mothers with high risk pregnancies.

8) Measurement of intraoperative organ specific blood oxygen saturation.

9) Provide an implantble real time pulse oximeter.

10) Identify ischemic areas of the brain. Unlike CT angiography, the present device will not need contrast material.

11) Acute, on nidus, monitoring of patients following stoke to prevent subsequent strokes.

Provided is an implantable pulse oximeter (oximeter A) that can be used to record hemoglobin saturation of oxygen in moving subjects. Such a device will provide the functionality of the immediate applications listed under applications (numbers 1-9) above and will be located outside a major blood vessel, embracing the vessel as will be further described herein.

A single plane fiber-optic sensor will be tested and miniaturized (Oximeter B). Such a device will be able to reach inner brain areas through an angiocatheter and identify potential ischemic areas. Presently there are no devices to measure potential stroke areas or to perform intracerebral post stroke monitoring. Oximeter B will provide applications 8-11. There is therefore an overlap of functions of oximeter A, B. According to the area of measurement either A or B will be selected by the clinician.

Although implantable on a blood vessel (Oximeter A) or within a blood vessel (Oximeter B), the device will still be non-invasive to the cerebral tissues.

Oximeter B will be useful to identify ischemic deep brain areas. Presently for that purpose, CT perfusion scans are used. A CT perfusion scan identifies areas under perfusion. However, areas under perfusion are not always ischemic due to collateral blood supply. Also, areas which are perfused may still be ischemic due to edema, collected material, etc. Therefore, a CT perfusion scan reading can be inaccurate. Use of contrast material can also be harmful for some patients, another shortcoming of CT perfusion scans. Above all, the CT perfusion scan method cannot be used for continuous post stroke measurements.

Another available option to measure cerebral oxygenation is the "Licox" probe. Due to its size (2-3 mm diameter), it cannot be passed via an interventional radiology route. Also it takes 20 min-2 hrs for the Licox probe to stabilize and then provide a reading. Therefore, it may not be the ideal solution for an acute stroke patient who has only only a two to four hour time window for intervention. A Licox probe is physically located within the brain area which will cause invasion of healthy tissue and subsequent traumas.

On the other hand, an intravascular pulse oximeter (B) of the present invention can be sent through the angiographic route to its desired destination. The device of the present invention will be devoid of the shortcomings of both the CT perfusion scan and the Licox probe method and will still meet the expectations of present stroke treatment regimens.

Oximeter B of the present invention will also have the light emitter as well as the receiver in the same plane.

Oximeters A and B will be able to monitor the oxygenation status of any organ of the body either during surgery or chronically. Oximeters A and B will also be helpful as diagnostic devices to identify ischemic areas. Therefore, although these devices are made to monitor stroke, they can be applied to monitor other organs as well.

The two devices of the present invention can be implanted either on a blood vessel (oximeter A) or within a blood vessel (oximeter B), to monitor tissue oxygenation levels.

The device according to the present invention is autoclavable in one embodiment. The emitter and sensor can be made overlapping to allow adjustment for the size of the blood vessel.

Monitoring blood oxygenation in the blood vessel, using the device on top of a vessel, will allow quick diagnosis of an impending stroke. If the blood oxygen levels of a distal artery are low, this is indicative of a proximal obstruction.

The present invention can be used to measure simultaneous major cerebral artery and vein oxygenation. The difference will be less if there is cerebral swelling (edema, stroke, bleeding). The device allows a practitioner to diagnose complications following traumatic brain injury. Presently, interventions are made in the presence of signs and symptoms only.

A pulse oximeter (A) is attached to a blood vessel near the site of a likely stroke, and is used to monitor large and medium size cerebral arteries. The device thus monitors large areas of cerebral tissues supplied by those arteries. Simultaneous application to an artery and a vein will allow quick diagnosis of cerebral swelling, bleeding, stroke, among other many common complications following traumatic brain injury.

Oximeter B can be passed within cerebral blood vessels to monitor the oxygenation status of the surrounding cerebral tissues. With oximeter B, the emitter and detector are coplanar and contained in a small area, e.g., 50-120 µm. Oximeter B can measure small areas of cerebral tissues located deep within the brain.

Both devices (A, B) can be useful to monitor any organ in the body either during surgery or chronically.

The output can be analyzed through suitable software.

Both devices (A, B) can send wireless signals to allow for chronic monitoring. Presently there is no device to measure cerebral oxygenation, chronically.

BRIEF DESCRIPTION OF THE DRAWINGS

Preferred embodiments will be set forth in detail with reference to the drawings, in which.

DESCRIPTION OF THE PREFERRED EMBODIMENTS

Figure 1:
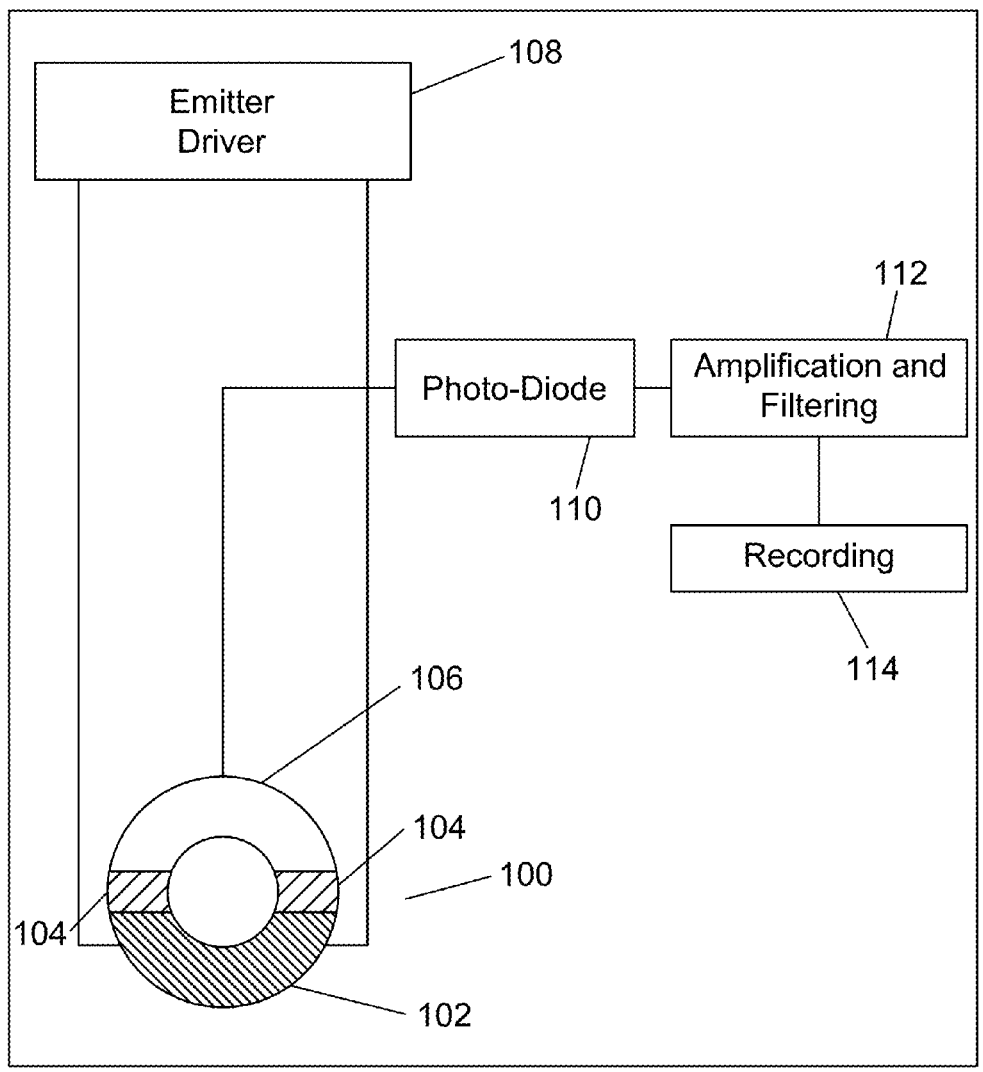
FIG. 1 is a diagram showing the basic circuitry of the oximeter according to a first preferred embodiment.

Preferred embodiments of the invention will now be set forth in detail with reference to the drawings, in which like reference numerals refer to like elements throughout.

FIGS. 1-6 show the first preferred embodiment, known as oximeter A.

FIG. 1 shows the basic circuitry of the extravascular oximeter 100. The oximeter 100 includes a light emitter 102, silicone cushions 104, and a photo receiving sensor 106 configured in a cylindrical shape to surround a vessel (not shown in FIG. 1). The emitter 102 operates under the control of an emitter driver 108 to emit light at two wavelengths, e.g., in the red and infrared ranges. An output of the photo receiving sensor 106 is made incident via fiber optics onto a photo diode 110, whose output signal goes to amplification and filtering circuitry 112 and recording circuitry 114.

Figure 2A:
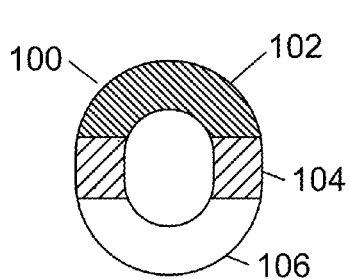
FIGS. 2A and 2B are diagrams showing cross-sectional views of the oximeter probe according to the first preferred embodiment.
Figure 2B:
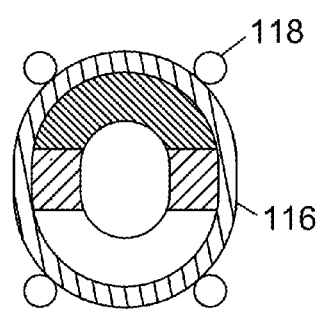

FIGS. 2A and 2B show the oximeter A cross section. A waterproof semicircular light emitter 102 and a light sensor 106 are provided. An outer covering 116 will embrace both the emitter and the sensor to keep them in place and protect them from moisture. Nylon hooks 118 will receive sutures, which will be used to attach the assembly to the body wall. The sensor will be tested initially while it is embracing the aorta as well as the inferior vena cava of 400-600 g Sprague Dawley rats.

Figure 3:
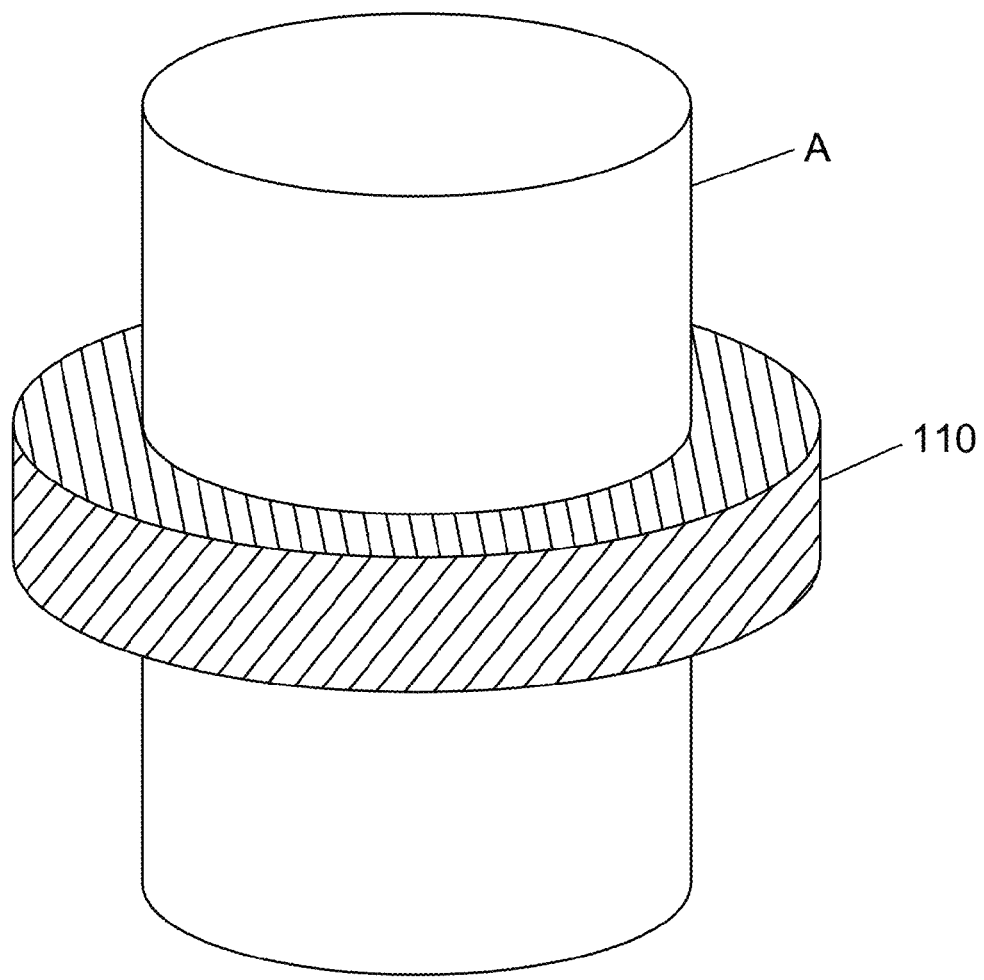
FIG. 3 is a diagram showing the manner in which the oximeter probe according to the first preferred embodiment surrounds the blood vessel.

FIG. 3 shows the sensor 100 wrapped around an aorta or inferior vena cava A.

Figure 4:
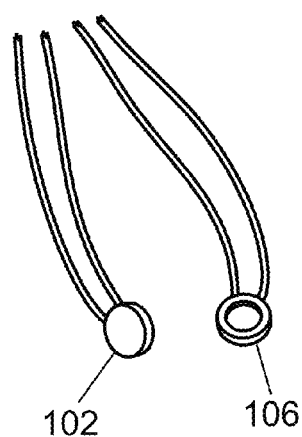
FIG. 4 depicts the emitter and sensor in an un-assembled state.

FIG. 4 shows the emitter 102 and the sensor 106 in an un-assembled state.

Figure 5:
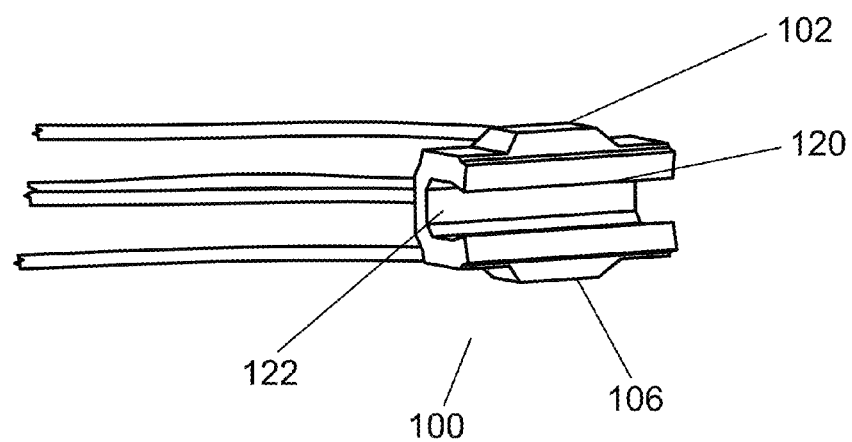
FIG. 5 depicts the emitter and sensor in an assembled state in a variation of the first preferred embodiment.
Figure 6:
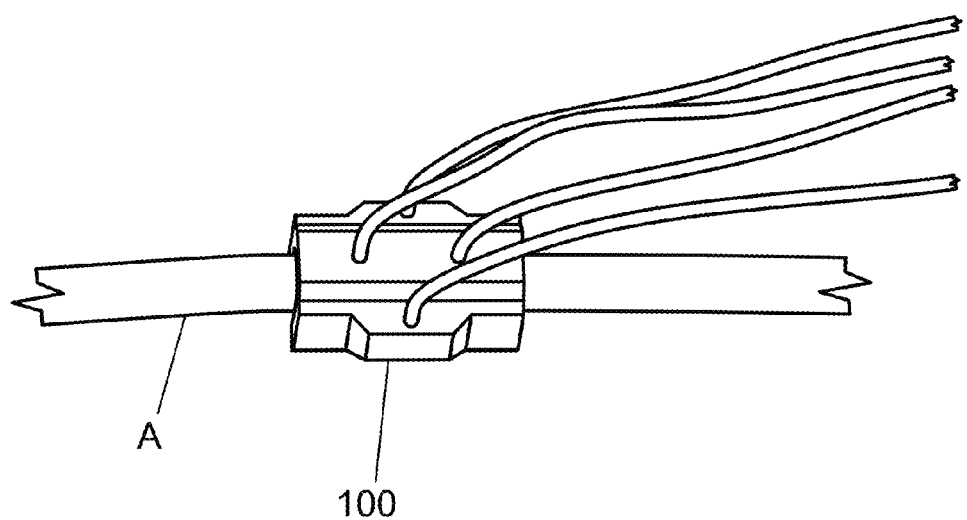
FIG. 6 depicts the probe of FIG. 5 attached to a blood vessel.

As shown in FIG. 5, the emitter 102 and the sensor 106 can be attached to a plastic tube 120, in which case the silicone cushions 104 are unnecessary. The plastic tube 120 has an opening 122 so that it can be clipped onto a blood vessel A, as shown in FIG. 6.

The emitter 102 has the ability to adjust to the light level automatically. Various intensities of light can be used, depending on the environment.

FIGS. 7A-9 depict a second preferred embodiment-oximeter B.

Figures 7A, 7B:
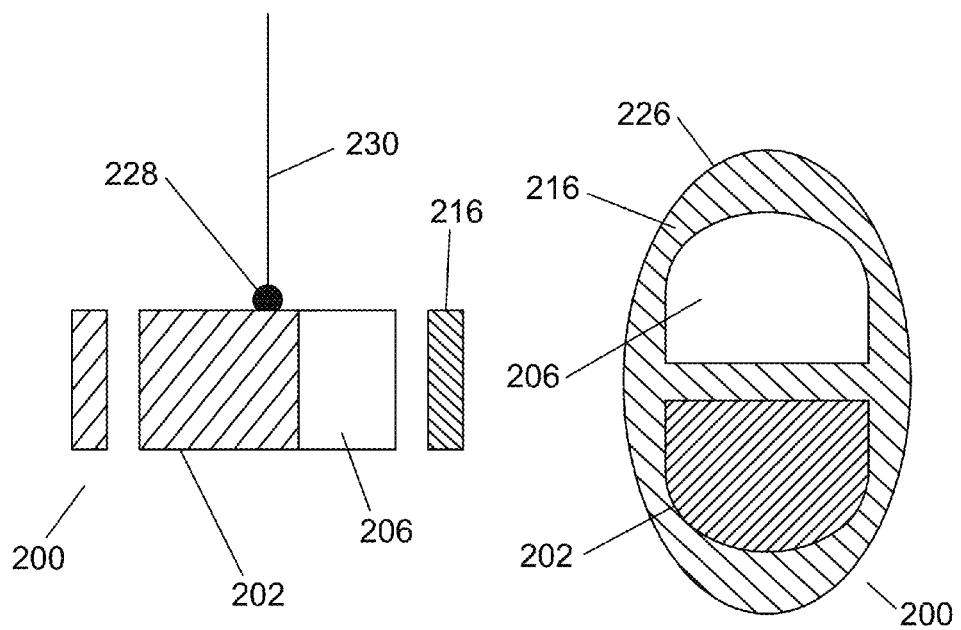
FIGS. 7A and 7B are diagrams showing the probe according to a second preferred embodiment.

FIGS. 7A and 7B show the second preferred embodiment, namely, the intravascular pulse oximeter (B) 200. The diameter of the sensor 200 will be in the range of 600 µm at the initial stage. At the final stages, the aim is to miniaturize its size to approximately 50 µm. This is feasible, as there are 125 µm fiber-optic oxygen sensors commercially available in the $100-300 range. With oximeter B, the light emitter 202 and the receptor 206 will be in the same plane. A rubber sleeve 216 will encase them both. A touch sensor 226 in the periphery will register sensor contact with the vessel wall. Biodegradable fibrin glue will be applied to the rubber sleeve, which will allow the sensor to be chronically placed. A ball and socket joint 228 allows the oximeter 200 to adhere to the vessel contour while providing a connection to a connecting cable 230.

Figure 8:
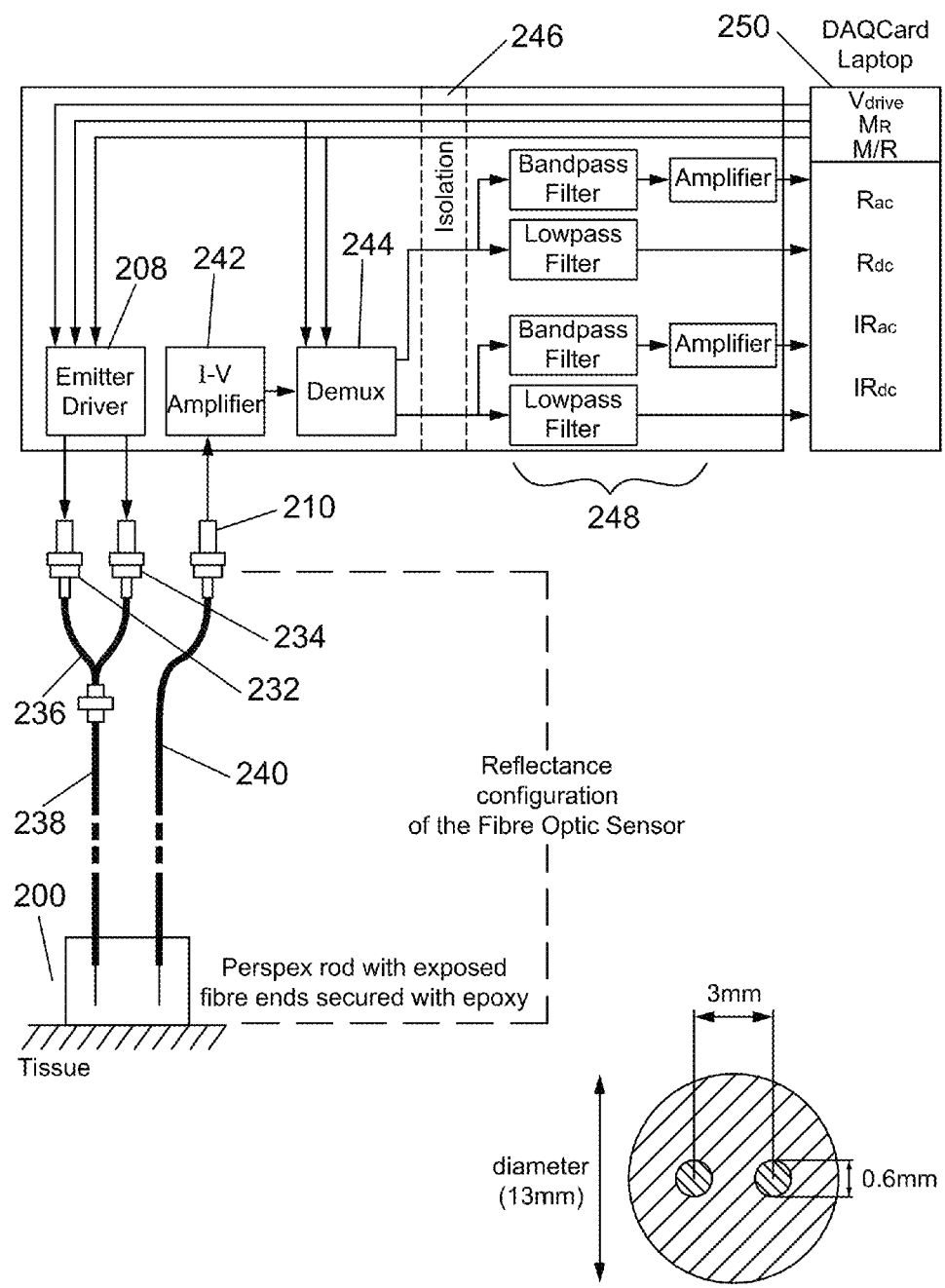
FIG. 8 is a diagram showing a fiber optic sensor pathway for use with the probe of FIGS. 7A and 7B.

FIG. 8 shows the basic fiber optic sensor pathway that will be used to record during phase 2 of the project. It was excerpted from Hickey, M et al., Journal of Clinical monitoring and computing (2011) 25:245-255; while it was not originally designed for an oximeter according to the present invention, it can be adapted for the oximeter B 200. An emitter driver 208 controls a red emitter 232 and an infrared emitter 234 to emit red and infrared light, respectively. Their outputs are combined by a Y piece 236 and input via a single transmitting fiber 238 into the oximeter 200. Light from the sensed area goes through a single receiving fiber 240 into a photodiode 210, whose output goes to a 1V amplifier 242 and a demux 244. The above components communicate via isolation 246 with filtering and amplifying circuitry 248 and a computing device 250. Similar circuitry can also be used for the oximeter A 100 of the first preferred embodiment.

Figure 9:
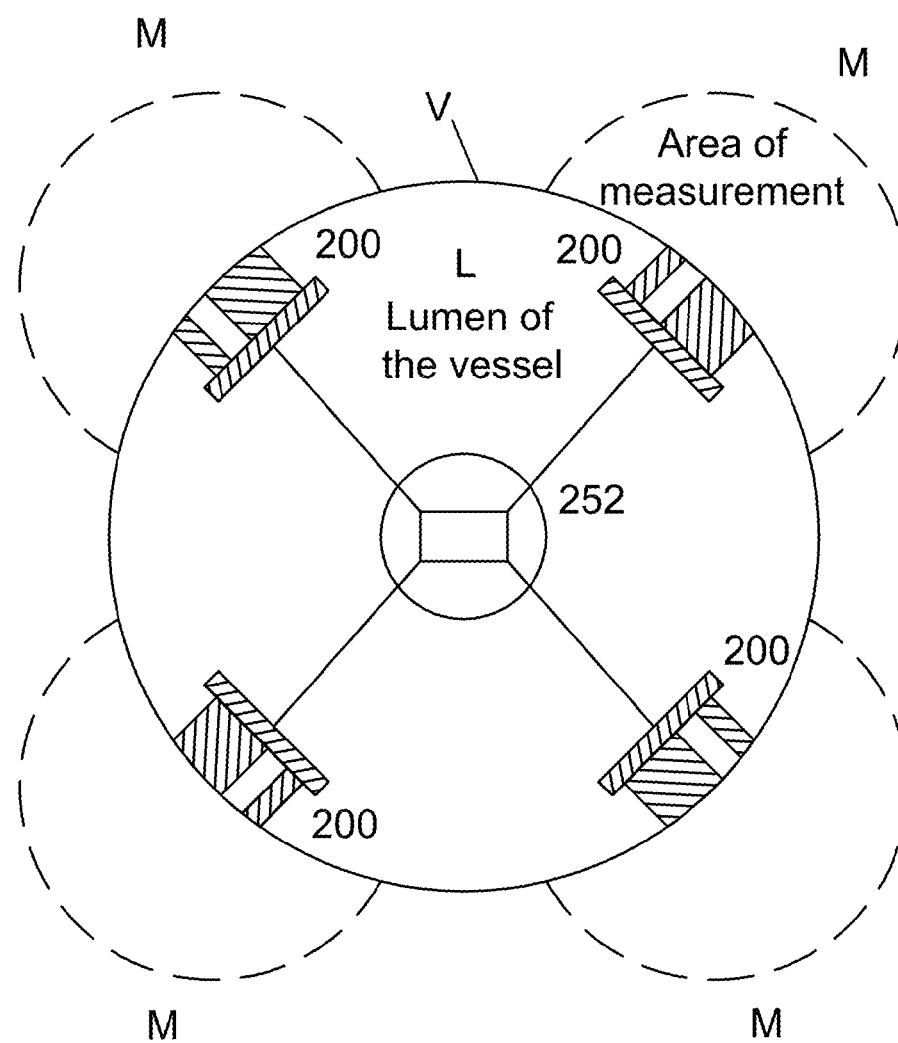
FIG. 9 is a diagram showing four probes according to the second preferred embodiment within a lumen of a blood vessel.

FIG. 9 shows four oximeters (B) 200 in action within a lumen L of a cerebral vessel V. Each sensor 200 obtains readings from tissues around the periphery of the blood vessel in an area of measurement M. This will allow for isolation of the area of ischemia. A few sensors can likewise be arranged to monitor a larger brain area, as shown in the figure.

The oximeter can be incorporated into a MERCI catheter or a Penumbra catheter to evacuate the thrombus at the same time. A common transmission line 252 is used. The output of the sensor is sent to a computing device to analyze the output to achieve any of the above ends. The computing device will be programmed with a suitable algorithm. The device will measure real time oximetry, heart rate, breath rate, breath distension and pulse pressure. Since the sensor and the light emitter are directly attached to a major blood vessel, the measurements will be very accurate and should not have artifacts such as those that are common in the above skin versions of oximetry presently used in clinical settings.

Figure 10:
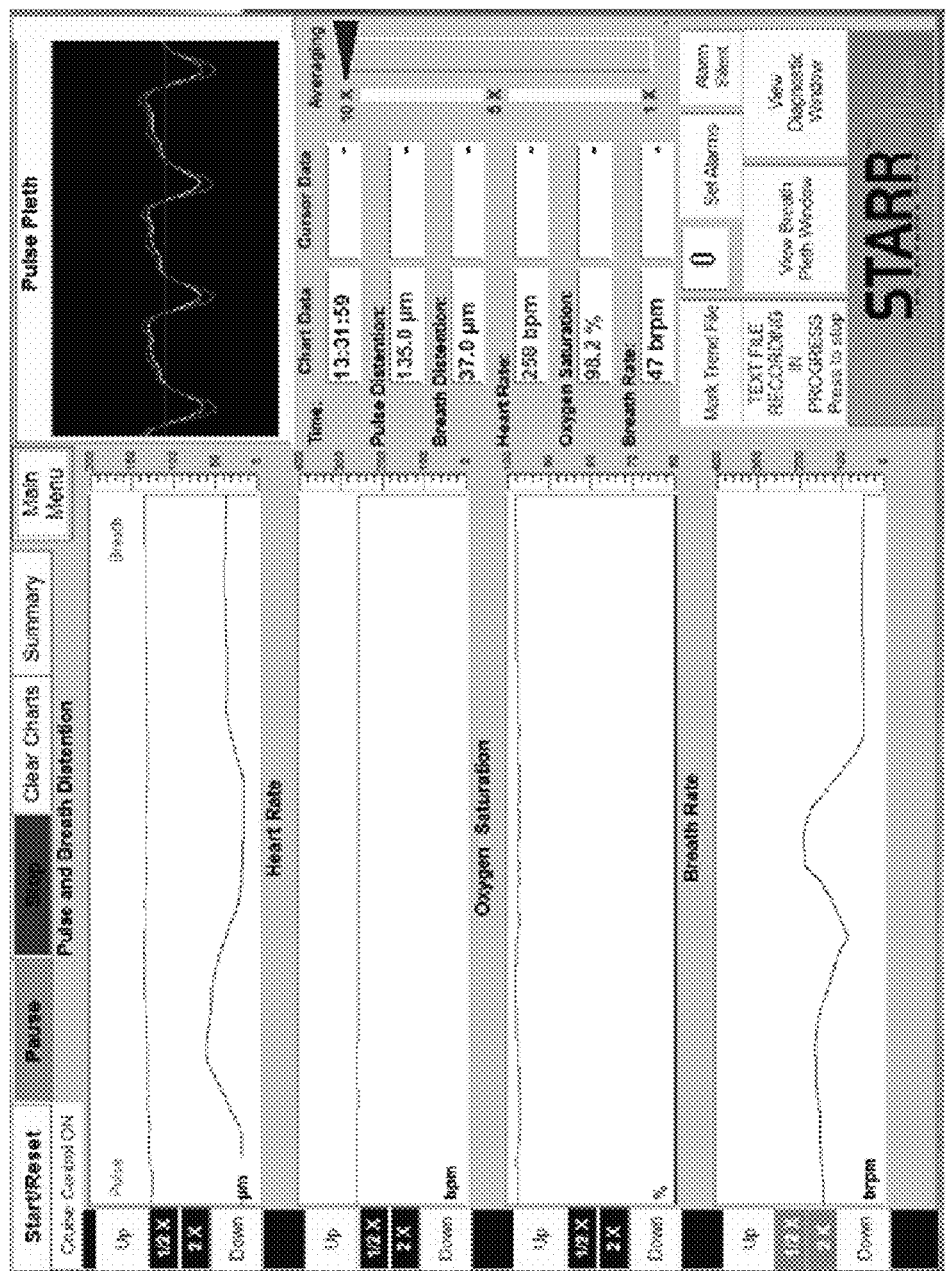
FIG. 10 is a screen image of device outputs.

FIG. 10 depicts a screen image of devie outputs.

The physiological parameters measured and their scientific basis are as follows. The oximeter provides real-time percent oxygen saturation of functional arterial hemoglobin.

Real-time cardiac pulse rate is given in bpm (beats per minute).

A real-time breath rate measurement is updated every few seconds. Note that this parameter is derived from respiratory effort, not airflow, and will be present even if the patient is experiencing an obstructive apnea, as long as breathing effort is present. Breath rate is given in breaths per minute or brpm.

Pulse distention is a measurement of the change in distention of the arterial blood vessels residing between the sensor pads due to a cardiac output pulse. It is a direct measurement of changes in local blood volume that accompany each cardiac pulse. Since the preferred embodiment records from the aorta, the readings are very accurate. For a given vascular compliance, pulse distention can also provide a surrogate for pulse pressure.

Pulse oximetry measures the oxygen content of arterial blood. The blood is identified as being arterial because of its pulsatile nature. That pulsation is identifiable because it causes a cyclic change in the absorption of light energy from the red and infrared LEDs (Light Emitting Diodes) as it passes through the vessel, due to the presence of changing quantities of blood that occur with every heart beat. Because the blood is arterial, it possesses systemic arterial oxygen content, which is measured. Pulse distention is simply a measurement of the change in the effective path length of the light that passes through only the arterial or pulsating blood, and it has true linear distance units of m.

One could envision this by theoretically placing all of the arterial blood residing in the light path between the sensor pads into a cylinder that has a cross-sectional area equal to the cross-sectional area of the column of the light beam passing from the LEDs to the photodiode. If the cylinder had one inlet and one outlet for the blood to enter and exit, then the level of blood in the cylindrical chamber would rise with each cardiac ejection stroke, and lower during each subsequent cardiac filling phase. The change in height of the blood in that cylinder between ejection and filling, or systole and diastole (Systolic BP-Diastolic BP), would then be measured directly as pulse distention.

The larger the pulse distention value, the more arterial blood will be available to make oximetry, as well as heart rate and breath rate, measurements.

Breath distention is a measurement of the change in distention of the arterial blood vessel residing between the sensor pads due to breathing effort. For a given vascular compliance, the breath distention provides a surrogate for intrapleural pressure.

While two preferred embodiments have been set forth above, those skilled in the art who have reviewed the present disclosure will readily appreciate that other embodiments can be realized within the scope of the invention. For example, recitations of numerical values, specific technologies, and specific materials are to be considered illustrative rather than limiting.

We claim:

1. An implantable extravascular pulse oximetry probe comprising:
    a red light emitter and an infrared light emitter configured in a semicircular shape and electrically coupled to an emitter driver circuit;
    a photo receiving sensor configured in a semicircular shape and optically coupled via fiber optics to a photo diode;
    the photo diode providing an electrical signal indicative of blood oxygen saturation values and pulse distention values;
    an attachment configured as a cylindrically shaped tube having a longitudinal opening for cylindrically attaching the red light emitter and the infrared light emitter and the photo receiving sensor around a blood vessel such that the attachment embraces the blood vessel and a transmission optical path is created through the blood vessel from the light emitters to the photo receiving sensor once implanted and placed on the blood vessel.

2. The probe of claim 1, further comprising cushions for separating the emitter from the detector.

3. The probe of claim 1, further comprising a covering around the red light emitter and the infrared light emitter and the photo receiving sensor.

4. The probe of claim 3, further comprising a hook attached to the cover for suturing the probe to tissue.

5. The probe of claim 1, wherein the red light emitter and the infrared light emitter and the photo receiving sensor are concave.

* * * * *